United States Patent [19]

Thottathil

[11] Patent Number: 4,625,038

[45] Date of Patent: Nov. 25, 1986

[54] (2S-TRANS)-4-SUBSTITUTED-2-PYRROLI-DINES-METHANOLS

[75] Inventor: John K. Thottathil, Trenton, N.J.

[73] Assignee: E. R. Squibb & Sons, Inc., Princeton, N.J.

[21] Appl. No.: 812,701

[22] Filed: Dec. 23, 1985

Related U.S. Application Data

[62] Division of Ser. No. 672,989, Nov. 19, 1984, Pat. No. 4,588,819.

[51] Int. Cl.$^4$ ............................................. C07D 207/08
[52] U.S. Cl. ..................................................... 548/570
[58] Field of Search ........................................ 548/570

[56] References Cited

U.S. PATENT DOCUMENTS

| | | | |
|---|---|---|---|
| 1,158,496 | 11/1915 | Hess | 548/570 X |
| 2,695,301 | 11/1954 | Blicke | 548/570 X |
| 2,708,194 | 5/1955 | Blicke | 548/570 X |
| 2,826,588 | 3/1958 | Feldkamp et al. | 548/570 X |
| 3,544,590 | 12/1970 | Kittleson | 548/453 |
| 3,636,043 | 1/1972 | Magerlein | 548/535 |
| 4,105,776 | 8/1978 | Ondetti et al. | 260/239 A X |
| 4,168,267 | 9/1979 | Petrillo, Jr. | 260/946 X |
| 4,337,201 | 6/1982 | Petrillo, Jr. | 548/413 |

FOREIGN PATENT DOCUMENTS

| | | | |
|---|---|---|---|
| 2520360 | 7/1983 | France | |
| 862868 | 3/1961 | United Kingdom | 548/570 |

OTHER PUBLICATIONS

Ponomarev, et al.; C.A., 86, 72344p, (1977).
Noritsina; C.A., 77, 139702p, (1972).
Ponomarev, et al.; C.A., 73, 109608n, (1970).
Ponomarev, et al.; C.A., 67, 32543d, (1967).
Silverman et al.; J. Organic Chemistry, vol. 45, pp. 815–818, (1980).
Saigo et al.; Chem. and Pharm. Bulletin, vol. 28(5), pp. 1449–1458, (1980).

*Primary Examiner*—Joseph Paul Brust
*Attorney, Agent, or Firm*—Lawrence S. Levinson; Donald J. Barrack

[57] ABSTRACT

Disclosed herein are novel chemical intermediates having the formula

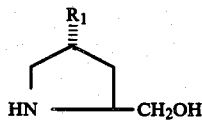

wherein $R_1$ is alkyl, cycloalkyl, aryl or arylalkyl.

3 Claims, No Drawings

(25-TRANS)-4-SUBSTITUTED-2-PYRROLIDINES-METHANOLS

This is a division of application Ser. No. 672,989, filed Nov. 19, 1984, now U.S. Pat. No. 4,588,819, issued May 13, 1986.

BRIEF DESCRIPTION OF THE INVENTION

Intermediates useful for the production of angiotensin converting enzyme inhibitors having the formulas

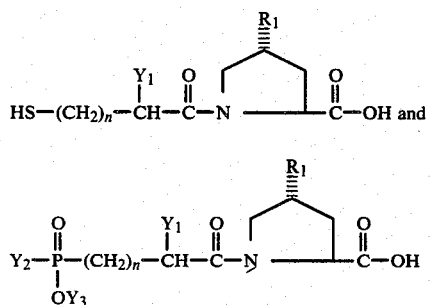

can be prepared by the process of this invention.

The process of this invention can be represented diagramatically as follows.

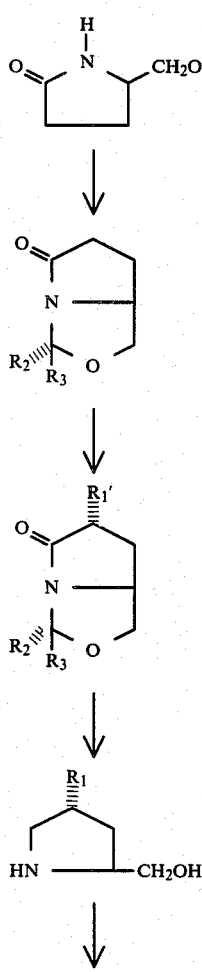

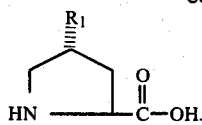

The compounds of formulas III, IV and V are novel, and as such, form an integral part of this invention.

In the above formulas, and throughout the specification, the symbols are as defined below.

$R_1$ is alkyl, cycloalkyl, aryl, or arylalkyl;
$R_1'$ is alkyl, cycloalkenyl, aryl or arylalkyl;
$R_2$ is alkyl, aryl, arylalkyl or cycloalkyl;
$R_3$ is hydrogen, alkyl, aryl, arylalkyl or cycloalkyl;
$Y_1$ is hydrogen or alkyl;
$Y_2$ is alkyl, aryl, arylalkyl, cycloalkyl, or (cycloalkyl)alkyl;
$Y_3$ is hydrogen, alkyl, arylalkyl, or

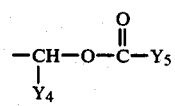

wherein $Y_4$ is hydrogen, alkyl or phenyl and $Y_5$ is hydrogen, alkyl, phenyl or alkoxy, or together $Y_4$ and $Y_5$ are $-(CH_2)_2-$, $-(CH_2)_3-$, $-CH=CH-$ or

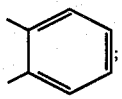

and
n is 0 or 1.

Listed below are definitions of the terms used in this specification. These definitions apply to the terms as they are used throughout the specification (unless they are otherwise limited in specific instances), either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to groups having 3 to 7 carbon atoms.

The term "aryl" refers to phenyl or phenyl substituted with halogen, alkyl, alkoxy, alkylthio, hydroxy, alkanoyl, nitro, amino, dialkylamino, or trifluoromethyl groups.

The term "alkanoyl" refers to groups having 2 to 9 carbon atoms.

The term "halogen" refers to fluorine, chlorine, bromine and iodine.

DETAILED DESCRIPTION OF THE INVENTION

The process of this invention is directed to the conversion of 5-hydroxymethyl-2-pyrrolidone (i.e., the compound of formula II) to a proline compound of formula VI.

The prolines of formula VI are useful as intermediates for the production of angiotensin converting enzyme inhibitors of formulas Ia and Ib. As described in the prior art, of which U.S. Pat. No. 4,105,776, issued Aug. 8, 1978, U.S. Pat. No. 4,168,267, issued Sept. 18, 1979, and U.S. Pat. No. 4,337,201, issued June 29, 1982 are representative, the angiotensin converting enzyme inhibitors of formulas Ia and Ib are useful for the treatment of hypertension in man. These compounds can be administered to a patient in need thereof as a single daily dose, or preferably as two to four divided daily doses.

The starting 5-hydroxymethyl-2-pyrrolidone of formula II is known; see, for example, Silverman et al., J. Org. Chem., 45: 815, (1980) and Saigo et al., Chem. and Pharm. Bull., 28(5): 1449 (1980). As described therein, it can be obtained from L-pyroglutamic acid by first esterifying the carboxyl group, and then chemically reducing the compound, using, for example, sodium borohydride, lithium borohydride or lithium chloride and sodium borohydride.

The process of this invention starts with the conversion of 5-hydroxymethyl-2-pyrrolidone to a compound having the formula

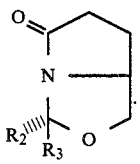
III

The conversion is accomplished by reaction of a compound of formula II with a ketone or aldehyde having the formula

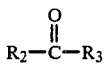
VII in the presence of an acid, preferably an organic acid such as p-toluenesulfonic acid. Alternative methodology is available and is shown in the examples.

The compound of formula III can be treated with a base, such as lithium amide (e.g., lithium diisopropylamide) or potassium hexamethyl disilazide and lithium chloride, and then alkylated with a compound having the formula

VIII wherein X is a leaving group such as halogen, methanesulfonyloxy, or toluenesulfonyloxy, to yield an alkylated compound having the formula

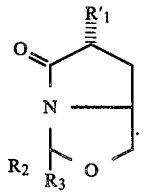
IV

In one embodiment of the invention, the compound of formula IV is isolated, and treated with a reducing agent, such as lithium aluminum hydride, diborane, diisobutylaluminum hydride, or the like, to reduce the oxo group and open the oxazole ring. Catalytic hydrogenation using, for example, palladium on charcoal as the catalyst is also needed if $R'_1$ is cycloalkenyl, to saturate the group. The resultant compound has the formula

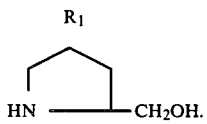
V

In an alternative embodiment of this invention, the compound of formula IV is not isolated, but is treated in situ with a reducing agent and subjected to catalytic hydrogenation (if needed) to obtain a compound of formula V.

In another alternative embodiment of this invention, a compound of formula IV is hydrolyzed to yield a compound having the formula

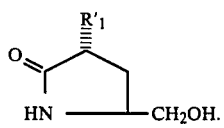
IX

Reduction of the oxo group of a compound of formula IX is accomplished with a reducing agent, such as lithium aluminum hydride, diborane, diisobutylaluminum hydride, or the like. Catalytic hydrogenation using, for example, palladium on charcoal as the catalyst, is also needed if $R'_1$ is cycloalkenyl, to saturate the group, and yield a compound of formula V. The hydrogenation can be run before, or after, the hydrolysis.

Conversion of the alcohol of formula V to a proline derivative having the formula

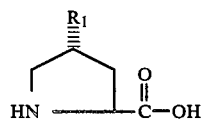
VI can be accomplished by oxidation. The preferred oxidation reaction is the Jones oxidation. This reaction comprises the addition of chromic anhydride in dilute sulfuric acid to a solution of the alcohol of formula V in acetone. Before proceeding with the Jones oxidation, it is preferable to protect the nitrogen atom of the pyrrolidine ring of a compound of formula IV with a conventional nitrogen protecting group, such as formyl, chloroacetyl, acetyl, benzyloxycarbonyl or t-butoxycarbonyl. The protection and deprotection (after the Jones oxidation) reactions are run using art-recognized procedures and will, of course, depend on the particular protecting group chosen.

Other oxidation procedures which can be used to convert an alcohol of formula V to a carboxylic acid of formula VI include: (i) catalytic oxygenation using, for example, platinum as a catalyst; (ii) treatment of the alcohol with oxalyl choride and dimethylsulfoxide followed by a hypochlorite, such as calcium hypochlorite; and (iii) treatment of an alcohol of formula V with pyridinium dichromate in dimethylformamide.

The following examples are specific embodiments of this invention.

EXAMPLE 1

Process for preparing (trans)-4-cyclohexyl-L-proline

(A)
(R)-Tetrahydro-3-phenyl-3H,5H-pyrrolo[1,2-c]oxazol-5-one

A mixture of 5-hydroxymethyl-2-pyrrolidone (85.0 g), benzaldehyde (98.0 g), p-toluenesulfonic acid (1.6 g) and toluene (500 ml) was heated to reflux using a Dean-Stark water separator and an oil bath, with vigorous stirring. After nine hours, the collection of water stopped and the cooled reaction mixture was washed with 5% sodium bicarbonate solution (2×50 ml), saturated sodium bisulfite solution (4×50 ml), water (2×50 ml) and brine (1×50 ml). The toluene solution was dried over anhydrous magnesium sulfate and the solvent removed on a rotary evaporator. The residue obtained was distilled, 145°–150° C./0.1 mm Hg to give the title compound as an oil (129.0 g). $[\alpha]_D = +269.6°$ (chloroform; c=1). TLC single spot at $R_f=0.5$ (silica gel, ethyl acetate-hexane; 4:1 UV and iodine).

Analysis Calc'd for $C_{21}H_{13}O_2N$: C, 70.92; H, 6.45; N, 6.89. Found: C, 70.97; H, 6.64; N, 6.72.

(B) (2S-trans)-4-Cyclohexyl-2-pyrrolidinemethanol

Diisopropylamine (68.2 ml) in dry tetrahydrofuran (500 ml) was cooled to −20° C. and n-butyllithium (178.6 ml, 2.73 molar) was added with stirring, keeping the temperature at about −20° C. After the addition, the solution was stirred for 15 minutes at −20° C. and cooled to −30° C. A solution of (R)-tetrahydro-3-phenyl-3H,5H-pyrrolo[1,2-c]oxazol-5-one (100 g) in tetrahydrofuran (200 ml) was added while maintaining the inside temperature at about −30° C. and the solution was stirred for 30 minutes. 3-Bromocyclohexene (82.0 ml) was added dropwise as a neat solution to the reaction flask at about −20° C. and the reaction mixture was stirred for 2.5 hours at that temperature. TLC showed no change afterwards; (silica gel, ethyl acetate-hexane: 4:1). The reaction mixture was transferred using a double ended needle to a vigorously stirred suspension of lithium aluminum hydride (23.5 g) in toluene at −10° C. After the addition, it was stirred for 15 to 20 minutes at −10° C. to control the reaction and the cooling bath was removed and the mixture refluxed for 30 minutes. The reaction mixture was cooled to −20° C. and saturated sodium sulfate was added dropwise, slowly and very carefully, until a gray granular precipitate was formed (40 ml solution). The reaction mixture was diluted with toluene (600 ml) and anhydrous sodium sulfate (100 g) was added, stirred well and filtered through a Celite pad. The filtrate was concentrated to a thick oil, diluted with 500 ml of toluene, and washed with water (2×300 ml) and brine (1×300 ml). The organic phase was concentrated and vacuum dried to yield 130 g of pale yellow thick oil. Part of the residue (123 g) was dissolved in ethyl acetate (150 ml) and diluted with 300 ml of acetic acid. Palladium on charcoal (10%, 20 g) was added to the acetic acid solution and the mixture was hydrogenated in a Parr shaker at 45 psi and at room temperature for about two hours. The reaction mixture was filtered and concentrated on a rotary evaporator and the residue was dissolved in 500 ml of water and basified using 30% sodium hydroxide solution with vigorous mechanical stirring. The precipitate (a cottony type material) was filtered, washed with 200 ml of water and air dried to yield 69 g of crude title compound. The filtrate and water washings on extraction with toluene yielded an additional 6 g of the title compound of equal quality. The combined material, on crystallization from toluene-hexane, yielded 50 g of the title compound, melting point 98°–100° C. TLC: single spot $R_f=0.5$; [silica gel ethyl acetate:acetonitrile:water:acetic acid; 4:4:1:1]. $[\alpha]_D = +12.85°$ (chloroform, c=1).

Analysis Calc'd. for $C_{11}H_{21}ON$: C, 72.08; H, 11.55; N, 7.64. Found: C, 71.87; H, 11.26; N, 7.32.

(C)
(2S-trans)-1-[(Benzyloxy)carbonyl]-4-cyclohexyl-2-pyrrolidinemethanol

To a solution of (2S-trans)-4-cyclohexyl-2-pyrrolidinemethanol (45 g) in tetrahydrofuran (400 ml) was added potassium carbonate solution (18.7 g, 120 ml water and cooled to −2° C. (Benzyloxy)carbonyl chloride (37.7 ml) was added dropwise to the well stirred reaction mixture, keeping the inside temperature between −2° and 0° C. After the addition (20 minutes), the reaction mixture was stirred for 15 minutes at 0° C. and poured into crushed ice and water (500 ml). The organic layer was separated after saturation with sodium chloride and the aqueous phase was extracted with ethyl acetate (3×100 ml). The combined organic phase was washed with 5% hydrochloric acid (2×100 ml), water (1×100 ml) and brine (1×100 ml). Evaporation of the solvents after drying over anhydrous sodium sulfate furnished a colorless thick oil, 78.1 g. TLC showed a single spot at $R_f=0.7$ with very faint shadow at origin and at solvent front (silica gel, ethyl acetate-hexane, 4:1, UV and iodine). $[\alpha]_D = 21.0°$ Analysis Calc'd. for $C_{19}H_{27}O_3N$: C, 71.89; H, 8.57; N, 4.41. Found: C, 71.88; H, 8.58; N, 4.37.

(D) (trans)-4-Cyclohexyl-L-proline

Method I

Crude (2S-trans)-1-[(benzyloxy)carbonyl]-4-cyclohexyl-2-pyrrolidinemethanol (78.1 g) was dissolved in 400 ml of acetone and added dropwise to a stirring solution of Jones reagent[1] (190 ml) in acetone (500 ml) at −5° C. After the addition (three hours), the reaction mixture was stirred for three more hours at −5° C. and isopropanol (30 ml) was added and stirred for 30 minutes. The top acetone layer was decanted and evaporated to a thick oil on a rotary evaporator at 30° C., mixed with the residue in the flask, diluted to 1500 ml with water and extracted using ethyl acetate (4×200 ml). The combined organic phase[2] was washed with brine, dried over anhydrous magnesium sulfate and the solvents removed on a rotary evaporator to yield crude title compound as a glassy solid (78.4 g). The product thus obtained was dissolved in methanol (600 ml) and palladium on charcoal (10%, 10 g) was added, and hydrogenated at ambient temperature and at atmospheric pressure (two hours). The white solid obtained on filtration and evaporation was powdered and suspended in 200 ml of warm ethyl acetate and filtered and washed with 200 ml ethyl acetate. The white solids thus obtained were vacuum dried to yield 41.8 g of product, melting point 250°–253° C. TLC showed a single spot at $R_f=0.3$, silica gel, ethyl acetate:acetonitrile:acetic acid:water (4:4:1:1) UV and iodine and Rydons reagent.

Note 1: Prepared by dissolving 26.7 g of $CrO_3$ in 23 ml concentrated $H_2SO_4$ and diluting to 100 ml with water.

Note 2. If the organic phase is brown colored at this point, it should be washed with saturated sodium bisulfite solution until the organic phase is colorless.

$[\alpha]_D = 30.3°$, (acetic acid, c=1).

Analysis Calc'd. for $C_{11}H_{19}O_2N$, partial hydrate of 0.35 water; C, 64.92; H, 9.75; N, 6.88. Found: C, 64.92; H, 9.55; N, 6.71.

Two grams of the product were dissolved in 10 ml of methanol, diluted to 100 ml using ethanol and concentrated until white solids started to precipitate (20 ml). The crystals were filtered, after cooling in the refrigerator for two hours, and washed with 50 ml of ethyl acetate and vacuum dried to furnish 1.8 g of product, melting point 265°–267° C.

$[\alpha]_D = -32.0°$ (acetic acid, c=1).

Analysis Calc'd. for $C_{11}H_{19}O_2N$, partial hydrate of 0.18 mole water: C, 65.87; H, 9.76; N, 6.98. Found: C, 65.87; H, 9.76; N, 6.71.

Method II

To a mixture of (2S-trans)-1-[(benzyloxy)-carbonyl]-4-cyclohexyl-2-pyrrolidinemethanol (0.65 g), sodium bicarbonate (0.5 g), dioxane (20 ml), and water (20 ml) was added freshly prepared platinum black (prepared by hydrogenating 0.3 g of platinum oxide). Oxygen was passed through the solution at room temperature for 16 hours with vigorous stirring. Filtration and acidification, followed by extractive work-up yielded (trans)-1-[(benzyloxy)carbonyl]-4-cyclohexyl-L-proline as a glassy solid. This compound can be deprotected using catalytic hydrogenation as described in Method I.

Method III

To a solution of (2S-trans)-1-[(benzyloxy)-carbonyl]-4-cyclohexyl-2-pyrrolidinemethanol (0.65 g) in dimethylformamide (10 ml) was added pyridinium dichromate (2.1 g). The mixture was stirred at room temperature for 16 hours and poured onto crushed ice and hydrochloric acid (25 ml). Extraction with ethyl acetate followed by solvent evaporation yielded 0.4 g of (trans)-1-[benzyloxy)carbonyl]-4-cyclohexyl-L-proline as a thick oil. The compound can be deprotected using catalytic hydrogenation as described in Method V.

EXAMPLE 2

Alternative process for preparing (trans)-4-cyclohexyl-L-proline (trans)-4-Cyclohexyl-L-proline was prepared from 5-hydroxymethyl-2-pyrrolidone using the procedure described in Example 1, but substituting the following methodology for preparing (2S-trans)-4-cyclohexyl-2-pyrrolidinemethanol from (R)-tetrahydro-3-phenyl-3H,5H-pyrrolo[1,2-c]oxazol-5-one:

Diisopropylamine (12.9 ml) in dry tetrahydrofuran (250 ml) was cooled to −20° C. and n-butyllithium (37.2 ml, 2.73 molar) was added with stirring, keeping the temperature at about 31 20° C. (R)-Tetrahydro-3-phenyl-3H,5H-pyrrolo[1,2-c]oxazol-5-one (18.7 g) in 50 ml of tetrahydrofuran was added to the solution at −78° C. and stirred for 30 minutes. 3-Bromocyclohexene (15.3 ml) was added as a neat solution at −78° C. and the temperature was brought to −20° C. and kept at that temperature for 2.5 hours. The reaction mixture was poured into crushed ice and water (about 300 ml), saturated with sodium chloride and extracted using ethyl acetate (3×100 ml). The combined organic phase was washed with ice cold 2% aqueous hydrochloric acid (2×50 ml), water (2×50 ml) and brine (1×50 ml) and dried over sodium sulfate. Removal of the solvent on a rotary evaporator gave 27.0 g of (3R-cis)-6-(2-cyclohexenyl)-tetrahydro-3-phenyl-3H,5H-pyrrolo[1,2-c]oxazol-5-one as a thick oil. TLC: silica gel, ethyl acetate-hexane showed a major spot at $R_f=0.65$ with shadows above and below. This crude material was used for the next step without further purification.

A solution of (3R-cis)-6-(2-cyclohexenyl)-tetrahydro-3-phenyl-3H,5H-pyrrolo[1,2-c]oxazol-5-one in tetrahydrofuran (5 ml) was added to a suspension of lithium aluminum hydride (0.2 g) in tetrahydrofuran (15 ml) and after the addition the mixture was refluxed for 30 minutes. Saturated sodium sulfate solution was added dropwise very carefully and slowly to the vigorously stirred ice cold reaction mixture until a gray granular precipitate was formed (about 1 ml). The reaction mixture was diluted with tetrahydrofuran (25 ml) and anhydrous sodium sulfate (about 10 g) was added, stirred well and filtered through a Celite pad. Evaporation of the solvents gave a thick oil (0.95 g), which was dissolved in 10 ml of ethyl acetate and diluted with 20 ml of glacial acetic acid. Palladium on charcoal (10%, 0.2 g) was added and hydrogenated in a Parr shaker at 45 psi. The workup procedure used was the same as in Example 1, and 0.34 g of analytically pure (2S-trans)-4-cyclohexyl-2-pyrrolidinemethanol was obtained.

EXAMPLE 3

Alternative Process for Preparing (trans)-4-Cyclohexyl-L-proline (trans)-4-Cyclohexyl-L-proline was prepared from 5-hydroxymethyl-2-pyrrolidone using the procedure described in Example 1, but substituting the following methodology for preparing (2-S-trans)-4-cyclohexyl-2-pyrrolidinemethanol from (R)-tetrahydro-3-phenyl-3H,5H-pyrrolo[1,2-c]oxazol-5-one:

Potassium hexamethyl disilazane (7.6 ml, 0.656 molar) was added to a suspension of lithium chloride (0.21 g) in dry tetrahydrofuran (10 ml) at −30° C. and stirred for 10 minutes, whereupon all the solids went into solution. A solution of (R)-tetrahydro-3-phenyl-3H,5H-pyrrolo[1,2-c]oxazol-5-one (1.0 g) in tetrahydrofuran (10 ml) was added and stirred for 30 minutes at −30° C. 3-Bromocyclohexene (0.9 ml) was added and the reaction mixture stirred for two hours at −20° C.; all the starting material was consumed. Extractive workup as in Example 2 furnished 1.40 g of (3R-cis)-6-(2-cyclohexenyl)tetrahydro-3-phenyl-3H,5H-pyrrolo[1,2-c]oxazole which was used for the next step without any further purification.

(2S-trans)-4-Cyclohexyl-2-pyrrolidinemethanol was prepared from (3R-cis)-6-(2-cyclohexenyl)tetrahydro-3-phenyl-3H,5H-pyrrolo[1,2-c]oxazole using the methodology described in Example 2.

EXAMPLE 4

Alternative process for preparing (trans)-4-cycloalkyl-L-proline (A)

(R)-Tetrahydro-3,3-dimethyl-3H,5H-pyrrolo[1,2-c]oxazol-5-one

Method I

A mixture of 5-hydroxymethyl-2-pyrrolidone (0.3 g) and 2,2-dimethoxypropane (2 ml) in dichloromethane was refluxed in the presence of a crystal (ca. 10 mg.) of p-toluenesulfonic acid for 20 hours. Aqueous extractive work up followed by solvent evaporation produced 0.18 g of (R)-tetrahydro-3,3-dimethyl-3H,5H-pyrrolo[1,2-c]oxazol-5-one as an oil (TLC showed a single spot at $R_f=0.6$ (ethyl acetate)).

Method II

A mixture of 5-hydroxymethyl-2-pyrrolidone (0.4 g), acetone (5 ml) and p-toluenesulfonic acid (ca. 10 mg) was refluxed in 20 ml of benzene for 20 hours with a Dean-Stark water separator. After working up the reaction mixture, distillation (boiling point 70°-75° C. at 0.5 mm of Hg) yielded 0.2 g of (R)-tetrahydro-3,3-dimethyl-3H,5H-pyrrolo[1,2-c]oxazol-5-one as an oil.

Method III

A solution of 5-hydroxymethyl-2-pyrrolidone (3.0 g) in 100 ml of dichloromethane was cooled in an ice bath and powdered cupric bromide (0.1 g) was added. 2-Dimethoxypropene (2.0 g) in 10 ml of dichloromethane was added dropwise and after the addition, the cooling bath was removed and the reaction mixture stirred at room temperature for 1 hour and at reflux for 3 hours. Extractive work up followed by distillation yielded 2.8 g of (R)-tetrahydro-3,3-dimethyl-3H,5H-pyrrolo[1,2-c]oxazol-5-one as an oil.

(B)
(3R)-6-(2-Cyclohexenyl)-tetrahydro-3,3-dimethyl-3H,5H-pyrrolo[1,2-c]oxazol-5-one To a solution of lithium diisopropylamide (prepared from 24.45 ml of diisopropylamine and 70.5 ml of n-butyllithium in 350 ml of tetrahydrofuran) was added 27.0 g of (R)-tetrahydro-3,3-dimethyl-3H,5H-pyrrolo[1,2-c]oxazol-5-one in 50 ml of tetrahydrofuran with stirring and cooling at −78° C. After stirring for 0.5 hour, 3-bromocyclohexene (29 ml) was added dropwise, and after the addition, the reaction temperature was increased to −10° C. Stirring was continued until the reaction ended (about 0.5 hour). Aqueous extractive work up yielded 4.15 g of (3R)-6-(2-cyclohexenyl)-tetrahydro-3,3-dimethyl-3H,5H-pyrrolo[1,2-c]oxazol-5-one as a viscous oil which showed a single spot on TLC at $R_f$=0.7 (ethyl acetate:hexane, 4:1).

(C)
(2S-trans)-4-Cyclohexyl-5-oxo-2-pyrrolidinemethanol

Method I (3R)-6-(2-Cyclohexenyl)-tetrahydro-3,3-dimethyl-3H,5H-pyrrolo[1,2-c]oxazol-5-one (5.8 g) was dissolved in 100 ml of ethyl acetate, 0.5 g of 5% palladium on charcoal was added, and the mixture was hydrogenated to yield (3R)-6-(cyclohexyl)-tetrahydro-3,3-dimethyl-3H,5H-pyrrolo]1,2-c]oxazol-5-one. This was dissolved in 50 ml of tetrahydrofuran and 20 ml of 20% hydrochloric acid was added. After stirring for one hour at room temperature, extractive work-up followed by crystallization yielded 4.0 g of (2S-trans)-4-cyclohexyl-5-oxo-2-pyrrolidinemethanol.

Method II (3R)-6-(2-Cyclohexenyl)-tetrahydro-3,3-dimethyl-3H,5H-pyrrolo[1,2-c]oxazol-5-one was hydrolyzed using 20 ml of 20% hydrochloric acid to yield (2S-trans)-4-(2-cyclohexenyl)-2-pyrrolidinemethanol which on hydrogenation (as in Method I) gave 4.0 g of (2S-trans)-4-cyclohexyl-5-oxo-2-pyrrolidinemethanol, melting point 96°-97° C.;
$[\alpha]_D^{25}$= +35.5° (c=1, chloroform).

Analysis Calc'd.: C, 67.01; H, 9.64; N, 7.11. Found: C, 66.76; H, 9.74; N, 7.04.

(D) (2S-trans)-4-Cyclohexyl-2-pyrrolidinemethanol

Method I

To a solution of lithium aluminum hydride (0.8 g) in 50 ml of tetrahydrofuran was added (2S-trans)-4-cyclohexyl-5-oxo-2-pyrrolidinemethanol (2.0 g) in 20 ml of tetrahydrofuran. After the addition, the mixture was refluxed for 24 hours, cooled to 0° C., quenched with ethyl acetate followed by saturated sodium sulphate solution, filtered, and the filtrate dried over anhydrous magnesium sulphate. Removal of the solvent followed by crystallization yielded 0.7 g of (2S-trans)-4-cyclohexyl-2-pyrrolidinemethanol as white crystals, melting point 98°-99° C.

Method II

To a solution of (2S-trans)-4-cyclohexyl-5-oxo-2-pyrrolidinemethanol (0.25 g) in 10 ml of tetrahydrofuran was added 0.37 ml of borane methyl sulfide, and the reaction mixture was stirred for 24 hours. The cooled reaction mixture was worked up using dilute hydrochloric acid followed by sodium hydroxide regeneration and yielded 0.2 g of crude product.

(E) (trans)-4-Cyclohexyl-L-proline

To a solution of Jones reagent (2 ml) was added sulfuric acid (0.5 ml) and acetic acid (2.5 ml). (2S-trans)-4-Cyclohexyl-2-pyrrolidinemethanol (0.5 g) in 5 ml of acetic acid was added to the above solution and after the addition, it was stirred at room temperature for 15 minutes. The reaction mixture was filtered through a Celite pad and washed with 10 ml of acetic acid. Isopropyl alcohol (2 ml) was added to the filtrate, stirred well, and a clear solution decanted and concentrated to a thick oil. The oil was dissolved in 5 ml of water and the pH was brought to 6.0 by the addition of concentrated ammonium hydroxide. The resultant precipitate was filtered, washed with 5 ml of water and excess ether, and vacuum dried to yield 0.42 g of (trans)-4-cyclohexyl-L-proline as a pink solid, which was crystallized from methanol to obtain colorless crystals.

What is claimed is:

1. A compound having the formula

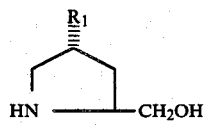

wherein $R_1$ is alkyl, cycloalkyl, aryl or arylalkyl;
the term "aryl" refers to phenyl or phenyl substituted with halogen, alkyl, alkoxy, alkylthio, hydroxy, alkanoyl, nitro, amino, dialkylamino, or trifluoromethyl groups;
the terms "alkyl" and "alkoxy" refer to groups having 1 to 10 carbon atoms;
the term "cycloalkyl" refers to groups having 3 to 7 carbon atoms; and
the term "alkanoyl" refers to groups having 2 to 9 carbon atoms.

2. A compound in accordance with claim 1 wherein $R_1$ is cycloalkyl.

3. The compound in accordance with claim 1, (2S-trans)-4-cyclohexyl-2-pyrrolidinemethanol.

* * * * *